(12) United States Patent
Cour

(10) Patent No.: US 6,397,955 B1
(45) Date of Patent: Jun. 4, 2002

(54) APPARATUS FOR EXPLORING THE SUBSOIL

(75) Inventor: Francis Cour, Lafitte (FR)

(73) Assignee: Racal Geodia (S.A.), Nanterre (FR)

( * ) Notice: Subject to any disclaimer, the term of this patent is extended or adjusted under 35 U.S.C. 154(b) by 0 days.

(21) Appl. No.: 09/125,355

(22) PCT Filed: Dec. 17, 1997

(86) PCT No.: PCT/FR97/02322

§ 371 (c)(1),
(2), (4) Date: Mar. 20, 2000

(87) PCT Pub. No.: WO98/27445

PCT Pub. Date: Jun. 25, 1998

(30) Foreign Application Priority Data

Dec. 18, 1996 (FR) .............................................. 96 15550

(51) Int. Cl.⁷ .............................................. E21B 19/14
(52) U.S. Cl. ...................... 175/52; 166/77.1; 242/613.2; 242/917
(58) Field of Search ............................ 52/108; 242/917, 242/613.2; 175/51, 52; 166/77.1

(56) References Cited

U.S. PATENT DOCUMENTS

| 4,166,508 A | 9/1979 | van den Berg ................ 175/20 |
| 4,572,304 A | 2/1986 | Mahar et al. ................... 175/5 |
| 5,174,389 A | * 12/1992 | Hansen .......................... 175/52 |
| 5,313,825 A | 5/1994 | Webster et al. ................. 73/81 |
| 5,584,351 A | * 12/1996 | Ellicott ......................... 175/62 |

FOREIGN PATENT DOCUMENTS

| EP | 2394796 | 1/1979 |
| JP | 574331 | 1/1982 |
| WO | 091019880 | * 12/1991 ................. 175/582 |

* cited by examiner

*Primary Examiner*—William Neuder
(74) *Attorney, Agent, or Firm*—Duane, Morris, LLP

(57) ABSTRACT

Apparatus for exploring the subsoil by means of a string of rods in which the bottom rod carries a tool, the rods being hinged to one another and being wound on a drum, which drum is moved in reciprocating rectilinear motion on a tower and is moved in rotary motion so as to enable successive rods to be lowered and subsequently to enable them to be wound back onto the drum.

14 Claims, 4 Drawing Sheets

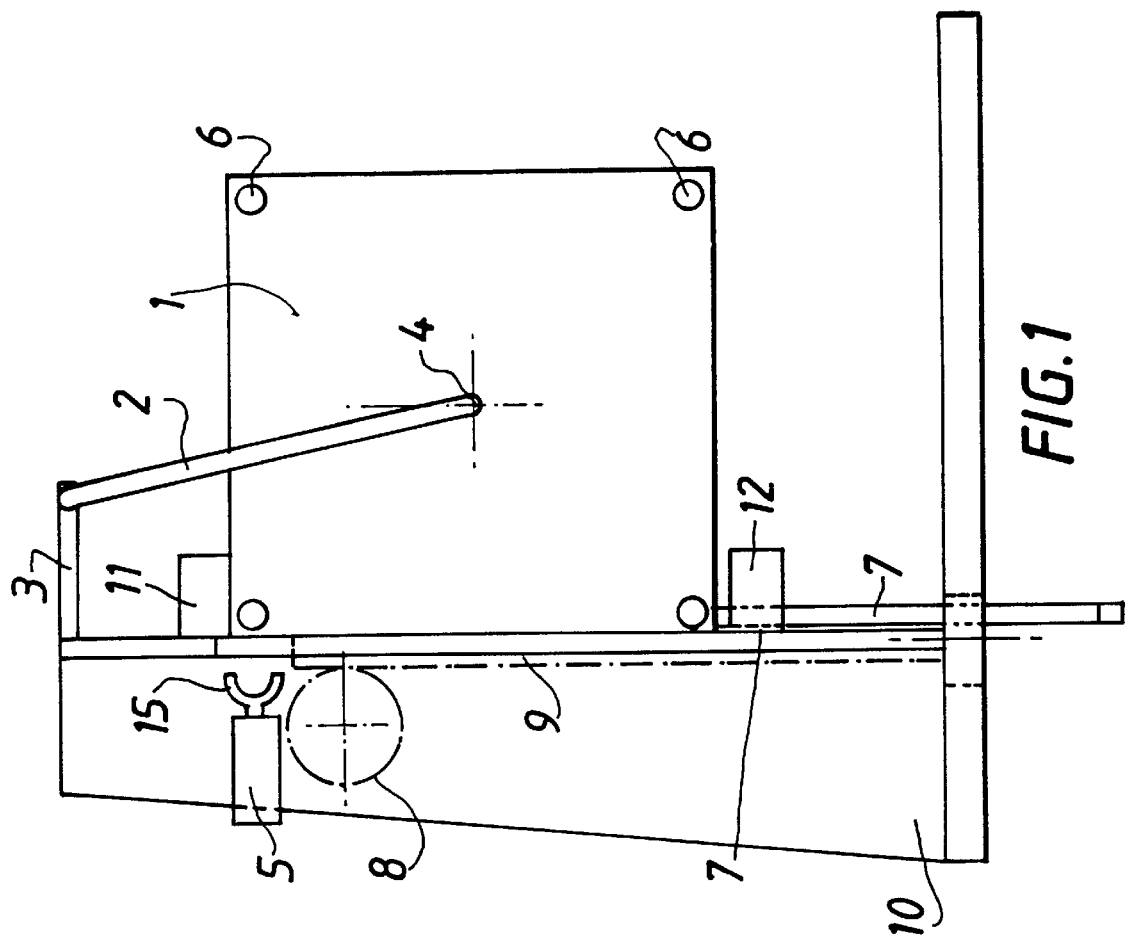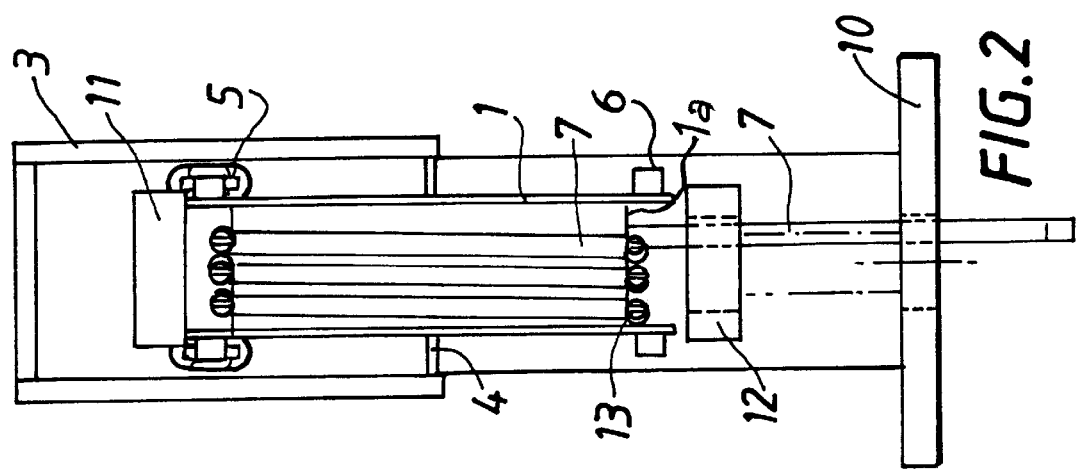

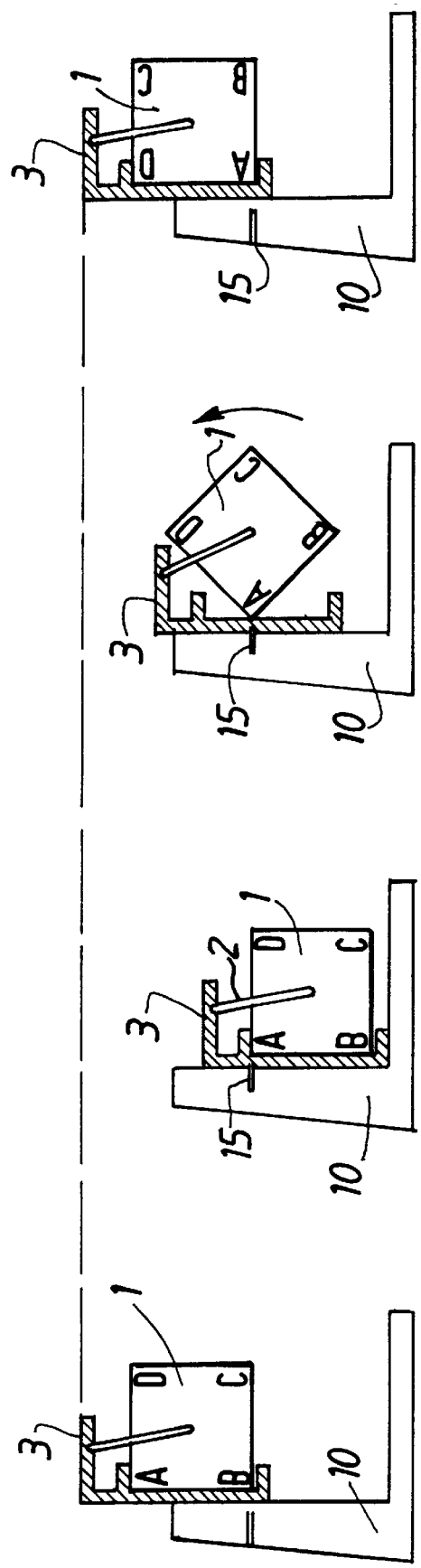

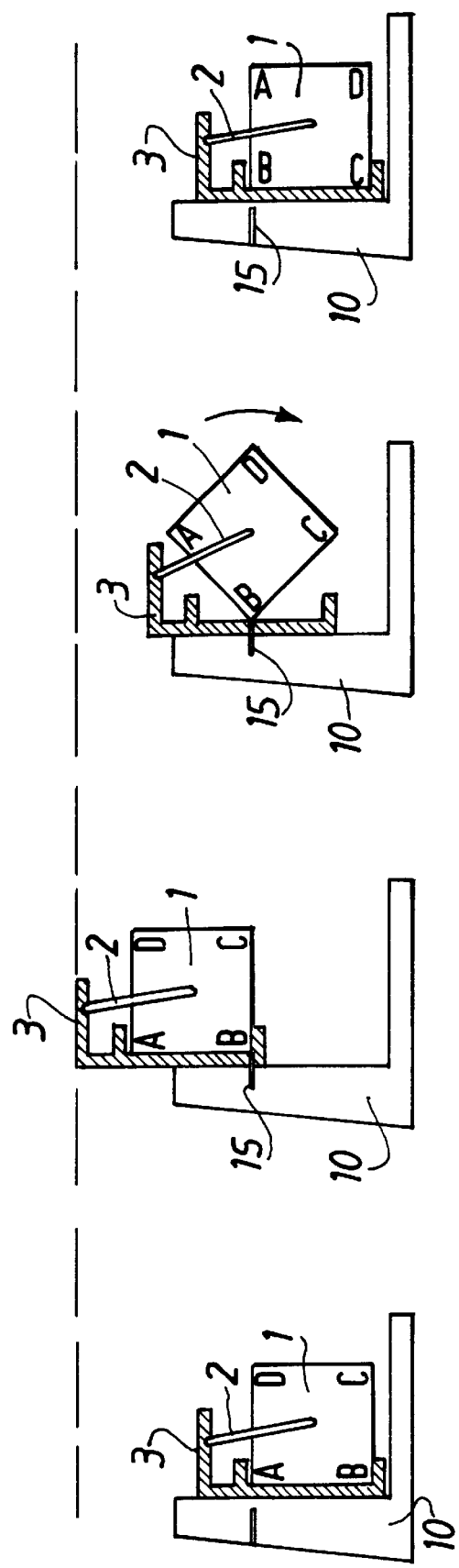

APPARATUS FOR EXPLORING THE SUBSOIL

The present invention relates to a penetration meter i.e. a device for performing underground exploration, and intended particularly, but not exclusively, for exploring the sea bed, at depths that may be as great as several tens of meters.

BACKGROUND OF THE INVENTION

One of the means commonly used for evaluating the mechanical characteristics of terrain that is to constitute the foundation of civil engineering work, is to perform static penetration testing, known as CPT.

The test consists of pushing a rod into the terrain concerned, which rod is fitted at its bottom end with sensors serving, throughout penetration, to measure continuously various parameters such as tip resistance and lateral friction.

These measurements are transmitted via a cable passing along a central bore in the rod. Conventionally, the rod is cylindrical and has a diameter of 36 mm. Penetration is performed at a continuous speed of 2 cm/sec. Investigation depth, and thus rod length, vary depending on circumstances over the range several meters to several tens of meters. The thrust force on the rod which is a function of the resistance of the terrain and of the depth of the investigation, commonly lies in the range several metric tons to 20 tons, above which value testing is normally stopped.

Thrust is generally exerted by means of an actuator acting on the top end of the rod. In practice, the rod is made up of successive elements that are screwed to one another. The length of each element does not exceed a few meters for practical reasons of actuator length and ability to withstand buckling under thrust force. Penetration is performed in steps, each step corresponding to the length of one element pushed by the actuator.

When investigating a site on land, the operations of connecting the elements end to end and of passing the measurement cable along the rod require manual operations to be performed, thereby presenting the drawback of significantly lengthening the time required for operation.

When investigating the sea bed, it is practically impossible to use manual intervention, so other modes of operation have been developed in order to eliminate the problem of connecting a string of rod elements together end to end. The one-piece rod, i.e. having a length that may be several tens of meters, is no longer thrust by applying an actuator to its end, but by means of a continuous thrust system using wheels. The two horizontal-axis wheels face each other and clamp the rod in facing grooves. Rotating the wheels makes it possible to apply a driving force. The drawback of such a system is associated with the clamping force that must be exerted by the wheels on the rod to develop the driving force. Given the mechanical characteristics of penetration meter rods, that system cannot be used for developing more than a few tons of thrust per pair of wheels. To reach the commonly-required twenty or more tons, several pairs of wheels must be stacked above one another.

A major drawback of that system results from difficulties associated with handling and using rods that are several tens of meters long, particularly for use in deep water.

To mitigate that drawback, proposals have been made to use the "coil tubing" technique which consists in winding the tube on a reel of large diameter. During the winding operation, the tube is subjected to plastic deformation. When performing the CPT testing, the tube is unwound progressively and is straightened out by a set of presser wheels, thereby subjecting it again to plastic deformation.

Such a system makes it possible to reduce problems associated with the space occupied by a one-piece tube, however the work-hardening to which the penetration meter rod is subjected during successive operations of being wound up and of being paid out and thrust into the ground, limits application to rods of small diameter for investigating shallow depths using forces of a few tons only, and in any event leads to the rapid deterioration of the tubes.

SUMMARY OF THE INVENTION

An object of the present invention is to mitigate those drawbacks and to make it possible to perform CPT type testing capable of penetrating to several tens of meters, using compact equipment that can be implemented automatically and that does not require manual intervention while testing is taking place.

According to the invention, the device for exploring the subsoil comprises a tower, mutually engageable rods, and means for applying pressure to a top end of the top rod of a string of rods, and the rods are hinged to one another and are disposed on a drum, the drum having a core of square section and of side equal to the length of a rod, the drum being carried by a bracket secured to a slider that is vertically movable in fixed guides, the drum carrying in the vicinity of its middle portion, a pair of claws or clamps that are retractable and that co-operate in succession with different ones of the corners of the square constituting the drum.

The string of rods is a continuous string, with the rods being hinged to one another. The string becomes rigid as the rods are brought successively into alignment. On the drum, the rods preferably rest side by side. Thus, pressure is always applied axially, thereby avoiding buckling, and secondly, guides are provided at the bottom portion of the tower.

Operation is as follows: after the tool has been fixed on one end of the first rod, the first rod is disposed vertically. The actuator presses on the second end thereof, thereby causing the tool to penetrate into the ground down to a depth equal to the length of the rod. Thereafter, the rod of the actuator is raised, thereby raising the bracket and likewise raising the drum. However the retractable claws situated beside the tower hold the top corner of the drum. As a result the drum rotates counterclockwise while it is being raised. This rotation through one-fourth of a turn brings the next rod which was previously in a horizontal position into a vertical position. During the next cycle, the clamps are retracted, the actuator lowers the drum, and the first rod together with the tool is pushed down into the ground by the second rod through a length equal to the length of one rod. These operations are continued until the desired depth has been reached.

The tool is raised in the opposite order, the clamps then preventing the corner that is at the bottom of the drum from rotating so as to prevent it from moving down, thereby obliging it to turn clockwise. The rods are thus put into place next to one another on the drum as they are raised.

It will be observed that no large force is exerted on the axis of the drum which need only support the weight of the drum plus the weight of the rods wound thereabout. Drive from the actuator is applied only to the rods, and only to the ends thereof.

BRIEF DESCRIPTION OF THE DRAWINGS

Other characteristics and advantages of the invention appear from the following description of particular embodiments, given solely as non-limiting examples, and with reference to the drawings, in which:

FIG. 1 is an elevation view of apparatus of the invention in a middle position;

FIG. 2 is an end view of the same apparatus;

FIGS. 4A to 4D are diagrams explaining the process for lowering a rod into the ground; and FIGS. 5A to 5D are diagrams for explaining the process of raising a rod.

DETAILED DESCRIPTION

Figure 3:
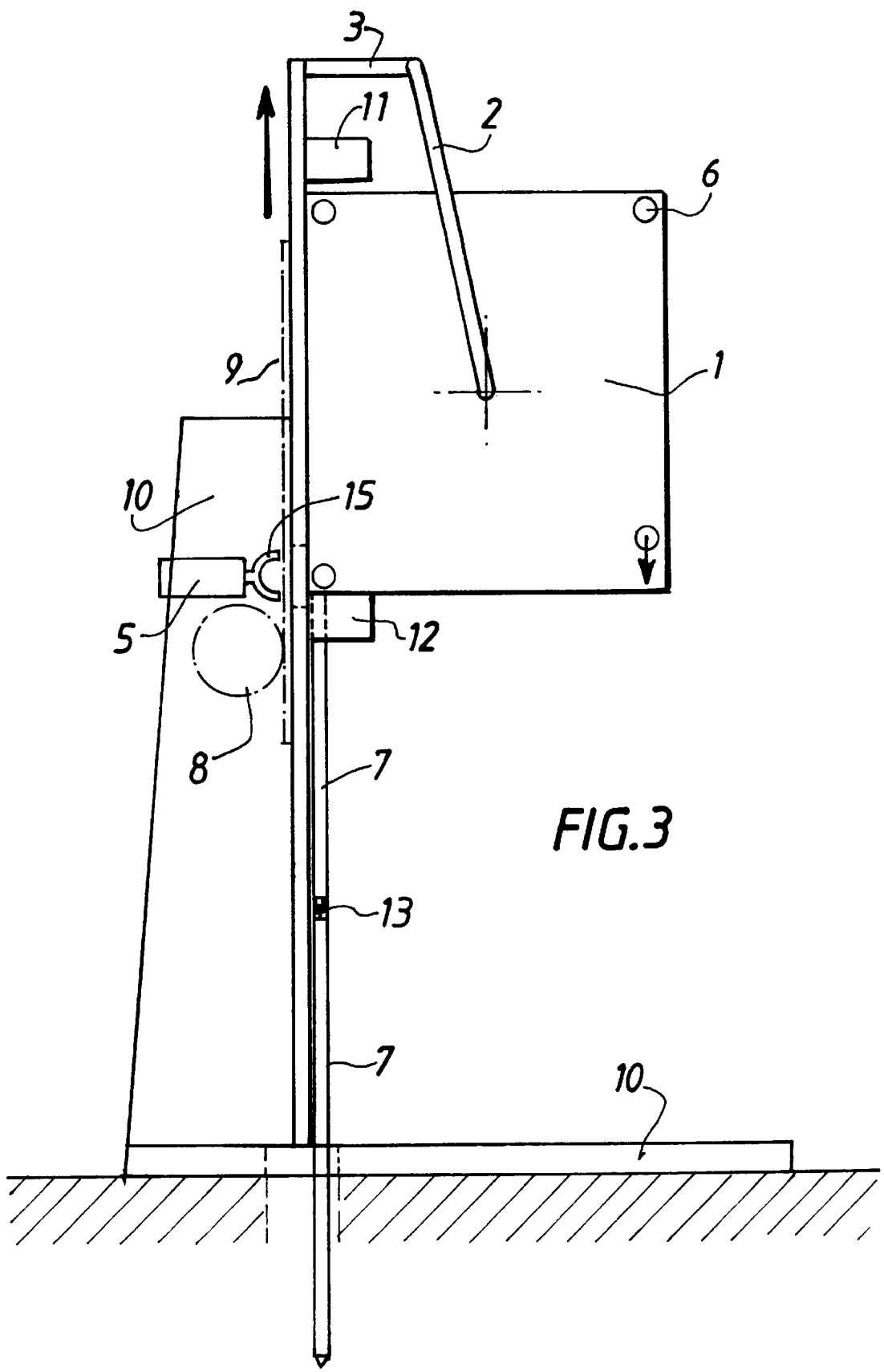
FIG. 3 is a view of the same apparatus in its high position.

In the example shown, drive comes from the action of a gear driven by a motor (not shown) on a sliding rack of a tower. However it would also be possible to provide a slider secured to the rod of one or more actuators. The stroke of the slider must be equal to twice the length of a rod. It is the slider which applies the pressure required for causing the tool to penetrate into the subsoil.

In FIG. 1, there can be seen the apparatus which comprises a structure resting on the ground, which may be constituted by the sea bed. The structure comprises a vertical tower 10 of relatively low height compared with the height of known apparatuses since its height is substantially twice the length of one rod, i.e. a maximum of 6 meters. At the top of said tower 10, there is provided a bracket 3 which, via two arms 2 (only one of which can be seen in FIG. 1) supports a drum 1. The arms 2 are hinged to the end of the bracket 3. The drum 1 has a core 1a of square section and is pivotally mounted on one (or two) shafts 4 rotatably secured to the bottom ends of the arms 2 which are themselves pivotally mounted relative to the bracket 3. In the position shown in FIG. 1, the drum 1 bears via one of its faces against the structure 10. This case applies when pressure is applied on a rod 7.

As can be seen in FIG. 2, the drum 1 receives a plurality of rods 7 on its core 1a, the rods being hinged one after another at 13 and are, so to speak, wound side by side on the core 1a of the drum 1. They are paid out and taken in by rotating the drum 1 about its axis 4. Inside the tower (FIG. 1) there is mounted a pinion 8 that meshes with a rack 9 which forms a slide, with rotation of the pinion 8 in one direction or the other causing the rack 9 to move up or down, with the bracket 3 being secured to the top end of the rack. Naturally, the rack is slidably mounted in vertical guides (not shown) of the tower or gantry. That is to say that rotating the pinion 8 causes the bracket 3 to move up or down. Two abutments 11, 12 form integral portions of the bracket. The pinion 8 is driven by a motor (not shown). However any other mechanical, electrical, pneumatic, or hydraulic means may be used to obtain reciprocating vertical motion of the bracket, and to obtain the pressure required for causing the tool and the rods to penetrate into the ground.

At each of its corners, the drum 1 has projecting studs or pegs forming pivots 6 when they come into contact with corresponding clamps 15. These pivots co-operate in succession with the corresponding clamps or forks 15 that are secured to the rods of actuators 5. Thus, the forks 15 can take up a projecting first position, each engaging one of the studs 6 to prevent the drum 1 from moving up or down, thereby causing it to rotate about the axis 4, while the forks have no effect when they are in the retracted, second position. Naturally, the drum 1 has four studs on either side and there are two actuators 5 on either side of the drum, as can be seen in FIG. 2.

FIG. 3 shows the apparatus in its high position. That is to say that under drive from the pinion 8, the bracket 3 has reached its top position. As the tool is lowered, the claw 15 remains in its retracted position and the rod remains vertical, which rod is still inside the drum and presses down on the rod immediately below it to transmit thereto the penetration force generated by the pinion 8 rotating clockwise. In contrast, when the string of rods is raised, the clamp 15 engages the stud 6 at the bottom of the drum, on the side of the tower, thereby preventing said drum from moving down. As a result, the drum turns through an angle of 90° in the clockwise direction about the stud 6, so that the corresponding rod 7 is laid on the drum.

The lowering of a rod element is described below with reference to FIGS. 4A to 4D. FIG. 4 are simplified diagrams showing only the structure 10, the drum 1, the bracket 3, and its hinged arm. In FIG. 4A, the drum is in its highest position as shown in FIG. 3. The four corners on one side of the drum 1 are identified by the letters A, B, C, and D. In FIG. 4B, the drum has been moved down as explained above under drive from a rack or an actuator, and it is in its lowest position. It has been moved through a distance equal to the length of one rod in vertical translation along the tower, and its corners are in the same disposition as in FIG. 4A. In this position, the actuator 5 engages the clamp 15 around the stud or peg 6 in corner A, thereby fixing the height thereof. Thereafter the rack and thus the bracket move back upwards, so the drum pivots counterclockwise with the drum axis moving outwards. At the end of this movement, the drum is in the position shown in FIG. 4D where the rod of the actuator 5 and the clamp 15 have again been retracted. The drum has turned through one-fourth of a turn, which corresponds to lowering one rod.

FIGS. 5A to 5D are diagrams showing how a string of rods is raised.

In FIG. 5A, the drum is in its lowest position. The clamp 15 is retracted. Under drive from the rack-and-pinion assembly, the bracket 3 and the drum 1 are moved in vertical translation to the position shown in FIG. 5B. This translation movement causes one rod 7 to be extracted from the ground. The clamp 15 is then advanced and holds the corner B of the drum, in the manner explained above. The bracket then moves back down, but the drum 1 is prevented from moving in translation by the clamp 15. As a result the drum turns about its corner B in the clockwise direction, with the arm 2 allowing it to move outwards to some extent. When the bracket 3 has returned to its lowest position, the drum has turned through one-fourth of a turn and one of the rods of the string has been wound on the drum. The corner B is released by retracting the clamp 15 and the cycle can begin again.

Rod hinge systems can lock automatically in a determined position and can unlock as soon as pressure stops being exerted, particularly by inserting tenons in slots or mortises of conventional design and that do not require any particular description.

The present invention thus makes it possible to provide a penetration meter that is simple to operate continuously. Its simplicity makes it possible to place it on a difficult-to-access sea bed and to operate it under remote control at great depth since cables suffice to deliver the power required from the surface and to return the data that is sensed.

The above description relates to a device for exploring the subsoil. However, the invention can naturally be used with other kinds of thrusted rod systems, e.g. for inserting a measurement cable or tube into the bottom of a preexisting borehole.

Naturally, numerous variants can be provided, in particular by substituting equivalent technical means, without thereby going beyond the ambit of the invention.

What is claimed is:

1. Apparatus for exploring a subsoil, the apparatus comprising a tower, a string of rods, means for applying pressure to a rod along the string of rods, and an exploration tool mounted at a bottom rod of the string of rods, wherein the rods along the string are hinged to one another and are placed on a drum with a square core having sides equal to a length of a rod, which core is mounted to rotate about a central axis.

2. The apparatus according to claim 1, wherein the drum is secured to a slide driven in reciprocating vertical motion in guides which are fixed to the tower.

3. The apparatus according to claim 2, wherein the drum is pivotally mounted by two arms on a bracket secured to the slide which is mounted to slide in the guides fixed to the tower, one end of each arm being pivotally mounted to the bracket, while an opposite end of said arm is coupled to the central axis of the drum.

4. The apparatus according to claim 1, wherein the tower has a pair of retractable clamps co-operating successively with each of four pairs of studs projecting from corners of the square core of the drum such that the drum pivots during an upward or a downward movement thereof on the tower.

5. The apparatus according to claim 3 wherein a reciprocating motion of the drum and a pressure for pushing down the rods and the tool are obtained by means of a pinion driven by a motor and meshing with a rack secured to the bracket.

6. The apparatus according to claim 4, wherein each said clamp is mounted on a rod of an actuator.

7. The apparatus according to claim 2, wherein the slide is driven by a rod of at least one actuator.

8. The apparatus of claim 1, wherein the rods are interfittable.

9. The apparatus of claim 1, wherein the means for applying pressure to said rod along the string of rods applies said pressure to an upper end of said rod when said rod is at the top of a part of the string extending downwardly to the bottom rod.

10. The apparatus of claim 9, wherein the means for applying pressure comprises means for vertically displacing the drum along the tower.

11. Apparatus for exploring below a surface, comprising:

a structure for resting against the surface;

a number of rods hinged together at ends thereof to form a string of rods;

an exploration tool carried on an endmost rod of the string of rods;

wherein the string of rods is carried on a drum with a square core having sides of a length equal to a length of a rod; and wherein the core is mounted to rotate about a central axis.

12. The apparatus according to claim 11, wherein the drum is carried on the structure by a slide driven in reciprocating vertical motion for extending and retracting the rods.

13. The apparatus according to claim 12, wherein the drum is pivotally mounted by two arms on a bracket secured to the slide, which is mounted to slide in guides fixed to the structure, one end of each arm being coupled to the bracket, and an opposite end of said arm being coupled to the central axis of the drum.

14. The apparatus according to claim 11, wherein successive corners of the drum are fixed relative to the structure during advance and retraction of the rods, whereby the drum pivots around the successive corners and rotates around the central axis during said advance and retraction.

* * * * *